United States Patent [19]

Johnson

[11] 4,377,554

[45] Mar. 22, 1983

[54] GENERATION OF MICROAEROPHILIC ATMOSPHERE

[75] Inventor: Raymond Johnson, Columbia, Md.

[73] Assignee: Becton, Dickinson and Company, Paramus, N.J.

[21] Appl. No.: 296,104

[22] Filed: Aug. 26, 1981

[51] Int. Cl.³ .............................................. B01J 7/00
[52] U.S. Cl. .................................... 422/239; 206/0.7; 422/236; 435/287; 435/801
[58] Field of Search ................ 422/86, 222, 236, 238, 422/239; 435/287, 801; 206/0.7, 532, 534

[56] References Cited

U.S. PATENT DOCUMENTS

| | | | |
|---|---|---|---|
| 3,246,959 | 4/1966 | Brewer | 422/236 |
| 3,419,400 | 12/1968 | Hayhurst et al. | 422/222 X |
| 3,483,089 | 12/1969 | Brewer | 435/287 |
| 4,003,709 | 1/1977 | Eaton et al. | 422/86 |
| 4,013,422 | 3/1977 | Spinner et al. | 422/236 X |
| 4,023,934 | 5/1977 | Spinner et al. | 422/86 |
| 4,033,826 | 7/1977 | Larsen et al. | 435/801 X |
| 4,200,610 | 4/1980 | Swaine et al. | 422/239 |
| 4,287,306 | 9/1981 | Brewer | 435/287 |

Primary Examiner—Richard L. Chiesa

[57] ABSTRACT

A gas generating package includes gas producing material present at a stoichiometric amount such that when contacted with water hydrogen is generated at a level sufficient to combine with a portion of the oxygen present in a closed container into which the package is placed. A catalyst for the hydrogen-oxygen reaction is provided exterior of the package. The package also includes a wick treated to permit introduction of water to the gas producing material at a predetermined level and rate.

6 Claims, 3 Drawing Figures

GENERATION OF MICROAEROPHILIC ATMOSPHERE

BACKGROUND OF THE INVENTION

This invention relates to gas generation, and more particularly to the generation of a microaerophilic atmosphere.

It is well known that some microorganisms require an aerobic atmosphere for growth whereas other microorganisms require an anaerobic atmosphere. Still other microorganisms, however, require an atmosphere having a predetermined level of oxygen falling between aerobic and anaerobic conditions, such atmospheric conditions are referred to herein as "microaerophilic atmospheres."

The attainment of an aerobic atmosphere is relatively simple, in most cases merely requiring aeration of the culture media. Anaerobic conditions are more difficult to attain and the prior art contains many devices and processes for producing anaerobic atmospheres. U.S. Pat. No. 3,246,959, discloses an apparatus for generating such anaerobic atmospheres and U.S. Pat. No. 3,483,089 discloses anaerobic apparatus for anaerobic culturing, which includes a cold platinum catalyst. In accordance with U.S. Pat. No. 3,246,959, there is provided a package which includes, for example, a material which is capable of generating hydrogen upon being contacted with water. The interior of the package is divided into two compartments, which are in fluid flow communication with each other, with one of the compartments including the hydrogen generating material. Upon introducing water into the other compartment, there is a controlled flow of water into the compartment containing the hydrogen generating material. Such package can be employed in an anaerobic jar such as disclosed in U.S. Pat. No. 3,483,089.

U.S. patent application Ser. No. 26,337, filed Apr. 2, 1979, now U.S. Pat. No. 4,287,306, describes a further apparatus for generating anaerobic atmospheres. In accordance with this patent application, a flexible sealed package is provided with a catalyst coated onto the exterior surface of the package for use in catalyzing the reaction between oxygen outside the package, and hydrogen generated from a hydrogen generating material within the package upon introduction of water into a compartment within the package.

In general, as described hereinabove, anaerobic conditions are attained by providing a closed container, a stoichiometric excess of hydrogen produced by a hydrogen generating material and a catalyst to cause reaction of the hydrogen with all of the oxygen in the container to form water. When faced with the problem of providing a microaerophilic atmosphere, the first thought of one skilled in the art of bacterial culture would be to use anaerobic gas generating apparatus and to reduce the amount of hydrogen generating material to the stoichiometric level required to cause reaction with only that portion of the oxygen which it is desired to remove. Such simple substitution of stoichiometric quantities of hydrogen generating materials in existing anaerobic apparatus, however, has not been wholly successful.

The present invention is directed to an improvement in such gas generating devices and to the provision of a gas generating device suitable for use in applications requiring a microaerophilic atmosphere.

SUMMARY OF THE INVENTION

In accordance with the present invention, there is provided an article for producing an atmosphere for use in providing a microaerophilic atmosphere. The article comprises a package, the interior of which includes a stoichiometric quantity of gas producing material which is capable of evolving a gas which reacts with gaseous oxygen to a predetermined extent. The package also includes a wick treated to permit introduction of water to the gas producing material at predetermined levels and rates suitable for providing the desired atmosphere. A catalyst for catalyzing reaction between oxygen and the gas generated within and released from the package is also provided.

In accordance with another aspect of the present invention, there is provided a carbon dioxide generating composition formulated in a manner to generate carbon dioxide and provide an acidic pH whereby, when used in a gas generating package along with a hydrogen generator, acidic to neutral pH conditions are maintained to thereby prevent carbon dioxide absorption which may occur under alkaline conditions.

More particularly, the carbon dioxide generating composition includes a water soluble solid acid and a water soluble solid carbonate in amounts suitable for generating carbon dioxide and also for providing an acidic pH; in particular, a pH of less than 6 when dissolved in water. As representative examples of suitable acids, there may be mentioned: citric, tartaric, ascorbic, succinic, malic, fumaric, lactic acids and the like. As representative examples of suitable carbonates, there may be mentioned: sodium bicarbonate, sodium carbonate, potassium carbonate, sodium sesquicarbonate, etc. The preferred composition includes citric acid and sodium bicarbonate. The composition is preferably employed in the form of a tablet in which suitable lubricants and binders are generally also employed. The exact proportions of acid and carbonate will differ with the materials used. The selection of suitable amounts to provide the desired carbon dioxide concentration for culturing and the acidic pH is deemed to be within the scope of those skilled in the art from the teachings herein.

THE DRAWINGS

The invention will be further described with respect to a preferred embodiment thereof; however, it is to be understood that the scope of the invention is not to be limited thereby. Such preferred embodiment is illustrated in the accompanying drawings, wherein.

DETAILED DESCRIPTION OF THE INVENTION

Figure 1:
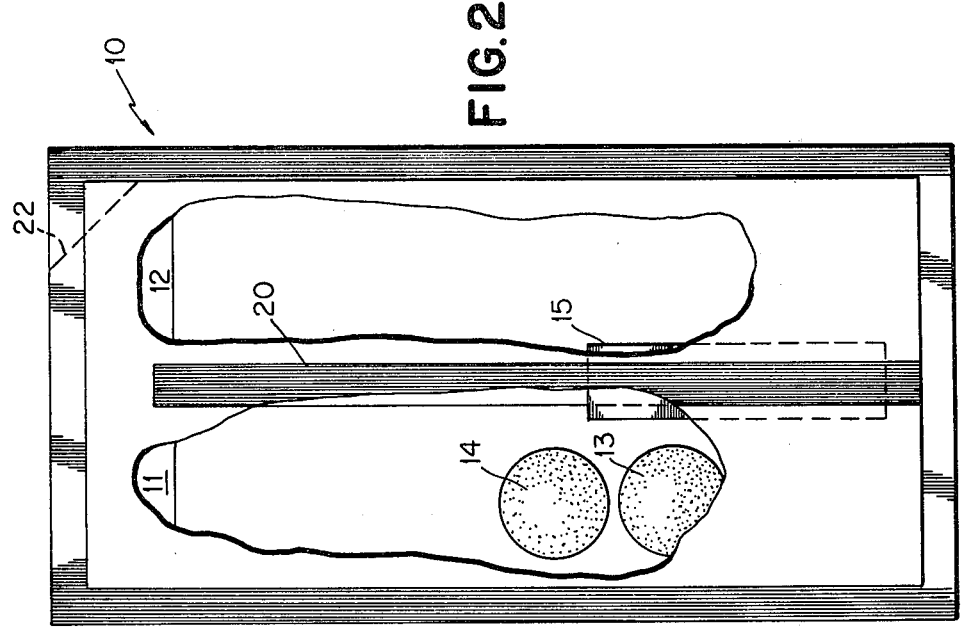
FIG. 1 is an elevational view of a preferred embodiment of a gas generating device in accordance with the invention.

Referring now to the drawings, there is shown a device for generating a microaerophilic atmosphere comprised of a package in the form of an envelope 10 made of a suitable material which is impervious to the atmosphere and moisture, and which is inert to materials contained within the package and gases generated therein and which is not destroyed by the heat of reaction released during use of the package, as hereinafter described. Thus, for example, the envelope 10 may be formed of a metallic foil, such as aluminum which is coated on its inner surface with a thermoplastic material, such as polyethylene or a polymer formed of vinyl chloride. The envelope 10 may be formed from two panels suitably secured together around the edges by heat sealing. In use, the envelope 10 is placed into container 101 having a lid 102 which forms a gas tight seal when the bracket 103 is tightened by the screw 104. The plated culture media in petri dishes 105 requiring a microaerophilic atmosphere are also placed in the container 101 prior to sealing the container. The closed container has a known volume of air and hence a known volume of oxygen. The volume of the package and a given number of petri dishes is also known and is accounted for in calculating the stoichiometric amount of hydrogen generating material required.

The interior of the envelope is divided into a first gas generating compartment 11 and a second liquid-receiving compartment 12 by a suitable partition 20 which is formed, for example, by heat sealing. The compartment 11 includes gas generating material in the form of a tablet 13, which includes materials capable of generating hydrogen and a tablet 14, which includes materials capable of generating carbon dioxide. The hydrogen generating material is present in a stoichiometric amount at a level sufficient to combine with from about 20 to about 80 percent of the oxygen present in the container. In general, based on sodium borohydride, the hydrogen generating material is used at a level of from about 0.15 gm to about 0.40 gm, preferably from about 0.20 gram to about 0.35, for generating a microaerophilic atmosphere in a 2.5 liter container.

The interior compartments 11 and 12 are in internal fluid flow communication with each other through a fluid transfer means in the form of a wick 15 (shown in phantom outline in FIG. 1 and FIG. 2) which is capable of permitting both liquid and gas flow between compartments 11 and 12. The wick 15 extends through the partition 20 into each of the compartments 11 and 12. As a result of the porosity of the wick, liquid and gas can slowly diffuse between the internal compartments.

Figure 2:
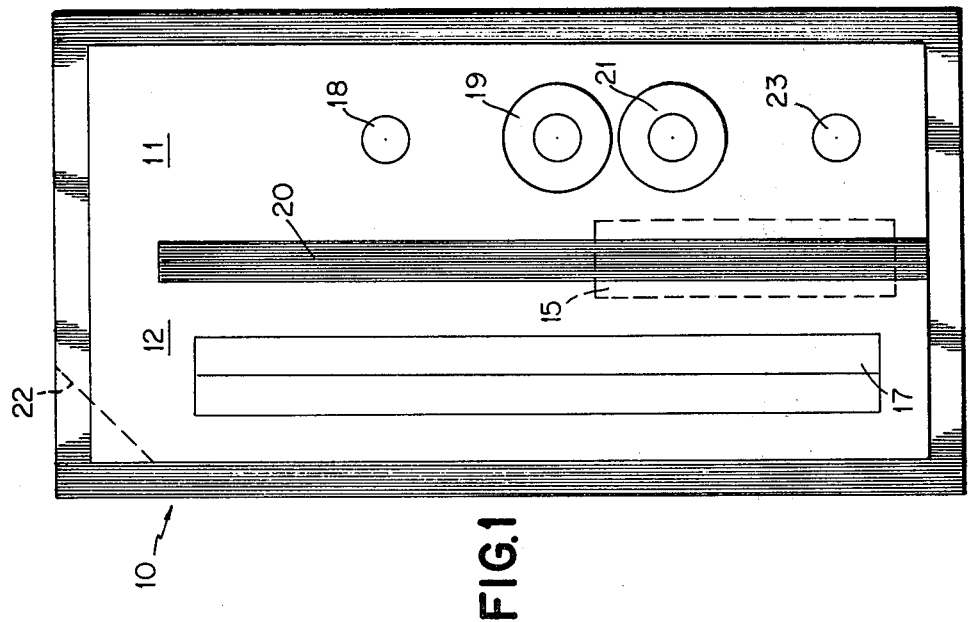
FIG. 2 is a cross-sectional view of the device of FIG. 1.
Figure 3:
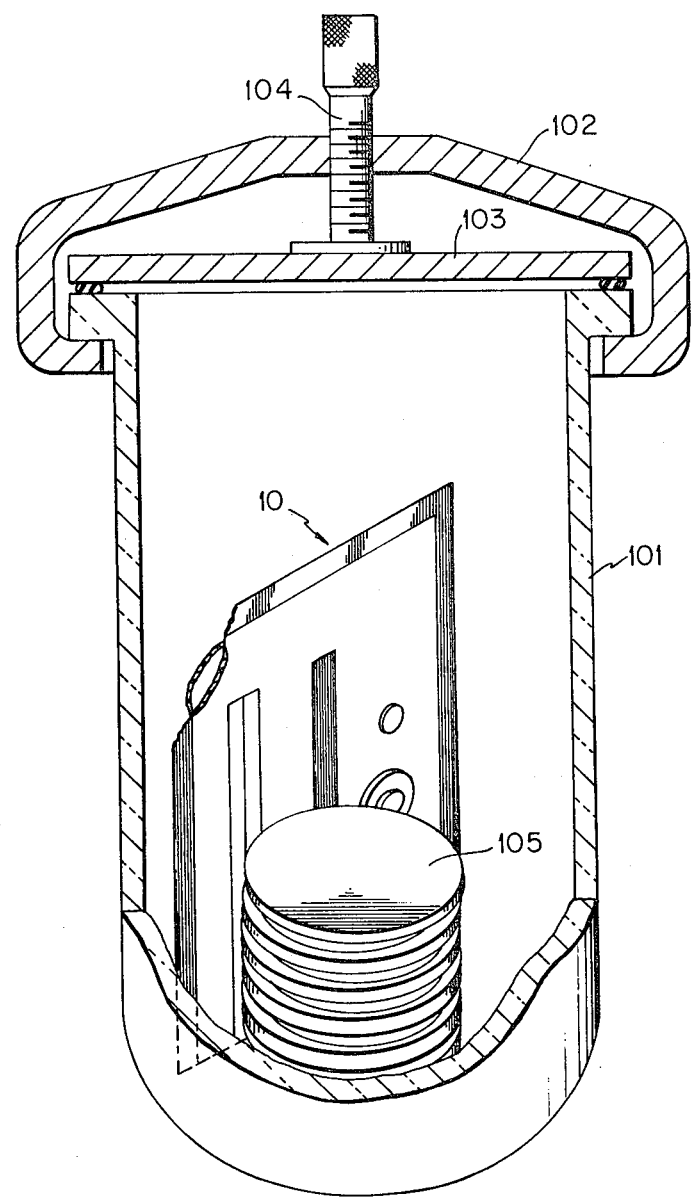
FIG. 3 is an elevational view of a jar employing the gas generating device.

It has been determined, however, that particular conditions of liquid and gas flow are required for effective generation of microaerophilic atmospheric conditions. As shown in FIGS. 1 and 2, the wick 15 extends across and through the partition 20 formed by heat sealing. There is, of course, incomplete sealing of the partition 20 at that portion overlying the wick 15, otherwise there would be no liquid and gas flow through the partition. It has been determined that variation and control of the pressure used during heat sealing of the partition 20 at that portion of the partition 20 overlying the wick 15 can be used to control the rate and volume of liquid and gas flow through the wick from compartment 12 into compartment 11. The control of the liquid and gas flow at predetermined levels provides the conditions necessary for successful generation of a microaerophilic atmosphere.

In general, two indicators of liquid and gas flow can be used to monitor and establish suitable conditions for generation of a microaerophilic atmosphere. The first indicator is the time after introduction of water into compartment 12 to establish liquid saturation of the wick (referred to herein as the "wetover time." The second indicator is the time after introduction of water into compartment 12 to produce the first liquid condensation in the gas generation compartment 11 (referred to herein as the "condensation time.") A wetover time of from about 1.5 to about 3 minutes and a condensation time of from about 10 to about 60 minutes is suitable. Preferred conditions are a wetover time of from about 2 to about 2.5 minutes and a condensation time of from about 20 to about 30 minutes.

Suitable, porous materials for use as wick 15 are filter paper, blotting paper, cotton twill, etc. A preferred wick material is filter paper having the designation Whatman #4. It should be understood that although the wick is shown as being a single sheet, it may be divided into two or more sheets. It should also be understood that the package need not be restricted to two compartments. As particularly shown, the partition 20 terminates before the top of the package whereby the compartments are in communication with each other above the partition. The package is designed to be used in a manner such that liquid introduced into compartment 12 does not reach a level above the partition whereby compartments 11 and 12 are only in gas flow communication above the partition.

In accordance with the present invention, a separate catalyst is provided or the exterior of package 10 is coated with a catalyst for catalyzing the reaction between oxygen and the hydrogen generated within and released from the package 10. As particularly shown in FIG. 1, such catalyst is coated on the metallic foil forming the exterior of package 10, with such catalyst generally being indicated as 17. It is to be understood that the catalyst could be applied other than by coating. In particular, such a catalyst could be comprised of palladium or platinum supported on a suitable support, such as carbon, aluminim oxide or other metal oxides which is then coated or otherwise applied onto the exterior of the package. Although the catalyst is generally shown in the form of stripes, it is to be understood that the catalyst may be applied in another form. The particular means for applying the catalyst to the package exterior is deemed to be within the scope of those skilled in the art from the teachings herein.

The provision of separate catalyst beads in a porous container depending from the lid of the jar is conventional and is not further described herein.

The catalyst is applied to the exterior of the package in an amount sufficient for catalyzing the reaction between hydrogen and a portion of the oxygen to thereby generate a microaerophilic atmosphere.

In accordance with a particularly preferred embodiment, an oxygen indicator is also applied to the exterior of package 10. Such an indicator may be coated or otherwise applied to the metallic foil, and such indicator, as particularly shown is in the form of three different indicators, generally indicated as 18, 19 and 21. The indicators may be of methylene blue, resazurin, and indigo carmine which respond to different levels of oxygen, or which have different oxidation-reduction potentials. The use of such indicators will indicate different levels of oxygen. A similar indicator for monitoring the level of carbon dioxide is also applied to the external surface of the metallic foil and is generally indicated as 23. Although such indicators have been particularly shown as being printed as spots on the exterior of the package, it is to be understood that the indicator may take other forms such as lettering or other designs.

As should be apparent, the package, in one embodiment, forms an integral unit for providing a microaerophilic atmosphere in that the package includes the materials for generating hydrogen and carbon dioxide, as well as the catalyst for catalyzing the reaction between hydrogen and oxygen and the indicators for indicating oxygen concentration and carbon dioxide concentration.

In employing the gas generating device of the present invention, the liquid receiving compartment 12 is opened by cutting away or tearing a corner of the package 10 along a tear line, generally indicated as 22. A material capable of interacting with the gas generating materials in compartment 11, such as water, is introduced into compartment 12, and such water flows into compartment 11, at a predetermined controlled volume and rate, through the wick 15. Upon contact with water, the tablets 13 and 14 generate hydrogen and carbon dioxide, which flows from compartment 11 into compartment 12 through the wick 15 and/or through the open upper channel, and ultimately into the container in which the envelope has been placed. The hydrogen reacts with oxygen in such container, with such reaction being catalyzed by the catalyst 17 applied to the exterior of package 10 or by a separate catalyst. In addition, oxygen conditions are indicated by means of the indicators 18, 19 and 21 which are applied to the exterior of package 10. Carbon dioxide concentration is indicated by indicator 23 which is also applied to the exterior of the package.

The invention will be described with respect to the following example; however, the scope of the invention is not to be limited thereby;

EXAMPLE

The following exemplifies a package in accordance with the present invention, which includes a carbon dioxide generating tablet, a hydrogen generating tablet, a catalyst for the reaction between hydrogen and oxygen applied to the exterior of the package and oxygen indicators and carbon dioxide indicators applied to the exterior of the package. The package in accordance with the example is employed as a gas generator, with such gas generation being effected by the addition of 10 ml of water to the liquid receiving compartment.

CARBON DIOXIDE GENERATING TABLET

| | |
|---|---|
| Citric Acid | 1.850 gm |
| Sodium Bicarbonate | 0.960 gm |
| In addition, the tablet includes suitable binder and lubricant; e.g., 0.1272 g talc 0.531 g microcrystalline cellulose | |

HYDROGEN GENERATING TABLET

| | |
|---|---|
| Sodium Borohydride | .27 gm |
| The tablet includes suitable binder and lubricants. The tablet can be coated with a water soluble gelatin to prevent decomposition. | |

FORMULATION OF CATALYST COATING 0.3333 g of Gum of Tragacanth
1.2 g of 5% carbon palladium catalyst.
Boil, cool and then shake mixture for uniformity.

FORMULATION OF INDICATOR BASE 18 g fructose
1.53 g K$_2$HPO$_4$
0.35 g NaOH
2.5 mg phenyl mercuric nitrate

FORMULATION OF METHYLENE BLUE INDICATOR

| | |
|---|---|
| 1.2 g Indicator base | Indicator Mixture |
| 5 mg methylene blue | |
| Weigh 1.2 g of dry indicator mixture with 0.3333 g Gum of Tragacanth. Add 40 ml of water and boil. Cool, ready for use. | |

FORMULATION OF INDIGO CARMINE INDICATOR

| | |
|---|---|
| 1.2 g Indicator base | Indicator Mixture |
| 5 mg indigo carmine | |
| Weigh 1.2 g of dry indicator mixture with 0.3425 g Gum of Tragacanth. Mix with 40 ml of water and boil. Cool, ready to use. | |

FORMULATION OF RESAZURIN INDICATOR

| | |
|---|---|
| 1.2 g Indicator base | Indicator Mixture |
| 5 mg of resazurin | |
| Weigh 1.2 g of dry indicator preparation with 0.3345 g Gum of Tragacanth. Add 40 ml of water and boil. Cool, ready for use. | |

FORMULATION OF CARBON DIOXIDE INDICATOR

| | |
|---|---|
| Sodium Bicarbonate | 0.02 g |
| Bromo Thymol Blue | 0.001 g |
| Gum of Tragacanth | 0.3333 g |
| Mix with 40.0 ml of water and boil. Cool, ready for use. | |

APPLICATION OF CATALYST

Apply sufficient catalyst coating to foil exterior to provide at least 0.001 g of palladium catalyst. Dry the stripe. The catalyst is ready to use.

APPLICATION OF INDICATOR

Methylene blue—Apply 1 drop (0.05 cc.) of indicator to exterior aluminum surface of package and dry.

Indigo carmine—Apply 1 drop (0.05 cc.) of indicator to exterior aluminum surface of package and dry.

Resazurin—Apply 1 drop (0.05 cc.) of indicator to exterior aluminum surface of package and dry.

PREPARATION OF PACKAGE

Two panels of aluminum measuring 5.9 inches by 3.3 inches were coated on one surface with vinyl laminate and were mated with the coated surfaces facing each other. Prior to mating the panels, the hydrogen generating tablet and the carbon dioxide generating tablet were emplaced between the panels in the position shown in FIG. 2. A rectangle of Whatman #4 filter paper measuring 3 inches by 1.2 inches was also emplaced in the position shown in FIG. 2.

The mated panels with tablets and filter paper in place were inserted into a heat sealing apparatus having mating platens in the configuration shown in shaded outline in FIG. 1. The platens were closed and the apparatus was activated to provide a pressure of 70±40 psig for 2-3 seconds and at a temperature of 250°-325° F. at the portion of the platens overlying the filter paper.

Subsequent measurements established that a wetover time of 2 minutes and a condensation time of 13 minutes were obtained under the sealing conditions described above. A microaerophilic atmosphere having 5-15 percent oxygen was established under these conditions with a container having a volume of 2.5 liters.

Although the invention has been described with respect to a preferred embodiment thereof, it is to be understood that numerous modifications are possible with the scope of the invention. Thus, for example, a liquid other than water could be employed for generating the gas, and tablets other than those particularly described could also be employed for generating gas. Thus, for example, a tablet capable of generating acetylene could be employed instead of a hydrogen generating tablet, although a hydrogen generating tablet is preferred. Similarly, the tablet could be formulated for producing hydrogen in a manner other than as particularly described; e.g., hydrogen could be generated by another liquid, such as an acid; in particular, hydrochloric acid, although the use of water is preferred. Similarly, the liquid for generating the gas upon contacting the tablet could be within the package in a separate compartment or ampoule. Thus, the present invention is not limited to the particularly described embodiment in that it is possible to provide a package which includes a material for generating hydrogen within the package, a catalyst on the exterior of the package in configurations other than the one particularly described and a catalyst separate from the package could be used.

These and other advantages should be apparent to those skilled in the art from the teachings herein.

Numerous modifications and variations of the present invention are possible in light of the above teachings and, therefore, within the scope of the appended claims, the invention may be practiced otherwise than as particularly described.

What is claimed is:

1. A unitary package for generating a microaerophilic atmosphere comprising
   (a) a flexible sealed package;
   (b) material in a first compartment of said package for generating hydrogen, said hydrogen generating material being present in a stocihiometric amount sufficient to generate hydrogen to react with from about 20 to about 80 percent of the oxygen of a gas tight container into which the package is inserted.
   (c) a second compartment in said package for receiving water, said second compartment being in fluid communication with said first compartment by means of a fluid channel; and
   (d) flow restricting means in said fluid channel for establishing predetermined wet-over and condensation times when said package is broken and water is inserted in said compartment, said wet-over time being from about 1.5 to about 3 minutes and said condensation time being from about 10 to about 60 minutes.

2. A package in accordance with claim 1 wherein said package is adapted for use in a 2.5 liter container and wherein said hydrogen generating material is present at a level of from about 0.15 gram to about 0.40 gram, on a sodium borohydride basis.

3. A package in accordance with claim 2 wherein said hydrogen generating material is present at a level of from about 0.20 gram to about 0.35 gram, on a sodium borohydride basis.

4. A package in accordance with claim 1 wherein said flow restriction means is filter paper.

5. A package in accordance with claim 4 wherein said filter paper is Whatman #4.

6. A package in accordance with either one of claims 1, 4 or 5 wherein said wet-over time is from about 2 to about 2.5 minutes and said condensation time is from about 20 to about 30 minutes.

* * * * *